(12) United States Patent
Forgash

(10) Patent No.: US 8,394,750 B1
(45) Date of Patent: Mar. 12, 2013

(54) ENCAPSULATED BATHTOY AND METHOD

(76) Inventor: Robin Forgash, Lighthouse Point, FL (US)

( * ) Notice: Subject to any disclaimer, the term of this patent is extended or adjusted under 35 U.S.C. 154(b) by 193 days.

(21) Appl. No.: 12/928,753

(22) Filed: Dec. 17, 2010

Related U.S. Application Data

(60) Provisional application No. 61/284,693, filed on Dec. 23, 2009.

(51) Int. Cl.
*A61K 8/02* (2006.01)
(52) U.S. Cl. .................... 510/141; 510/144; 510/152
(58) Field of Classification Search .............. None
See application file for complete search history.

(56) References Cited

U.S. PATENT DOCUMENTS

| | | | |
|---|---|---|---|
| 2,677,913 A | 5/1954 | Swartz | |
| 3,680,250 A | 8/1972 | Hetrick | |
| 4,881,915 A | 11/1989 | Liaw | |
| 5,273,476 A | 12/1993 | Dorfman | |
| 6,720,296 B1 * | 4/2004 | Bitton | 510/141 |

* cited by examiner

*Primary Examiner* — Necholus Ogden, Jr.

(57) ABSTRACT

A water soluble membrane comprising of liquid soap or bath oils encapsulating a figurine or toy. The figurine or toy floats freely in the liquid soap or bath oils that have been fully encapsulated by a water soluble membrane. The figurine or toy will be visible or concealed from the outer water soluble membrane that contains a clear or tinted in color, transparent liquid soap or bath oils. The water soluble membrane dissolves leaving a toy or figurine and bath bubbles or a bath soak once it has been placed in the bath water.

6 Claims, 1 Drawing Sheet

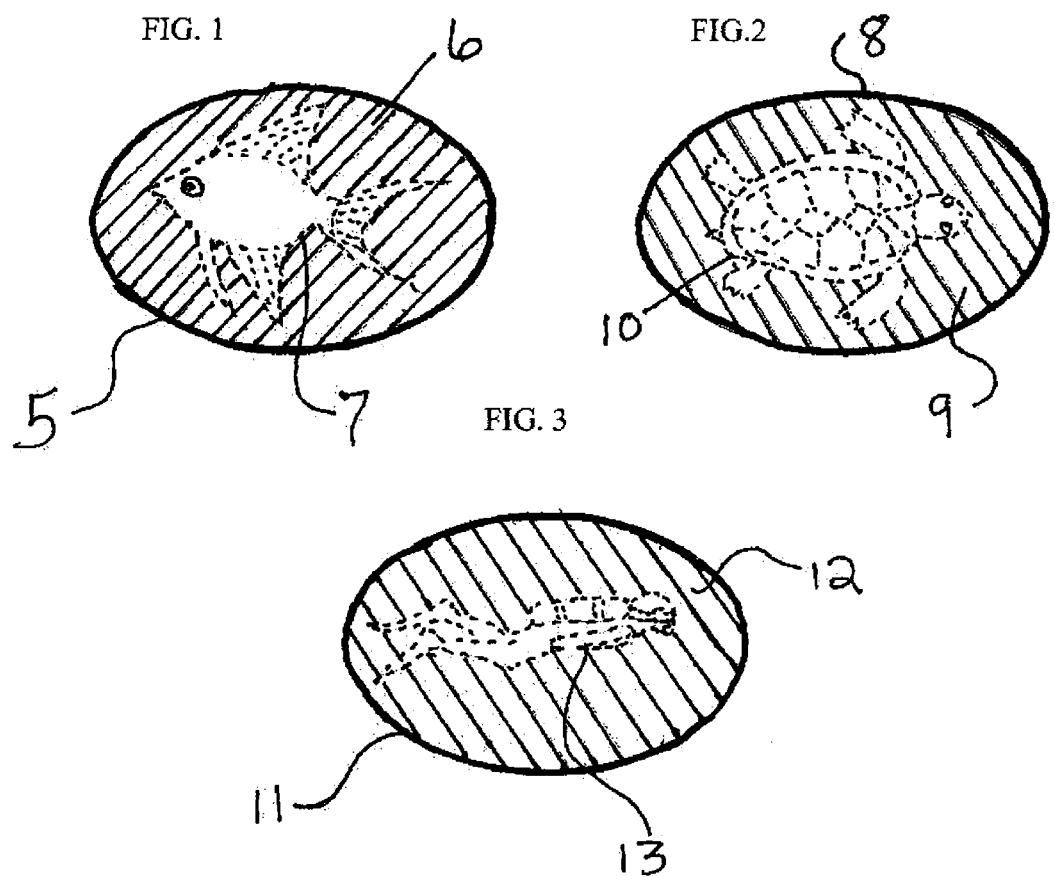

ENCAPSULATED BATHTOY AND METHOD

CROSS-REFERENCE TO RELATED APPLICATIONS

This application claims the benefit of provisional patent application Ser. No. 61/284,693, filed 2009 Dec. 23 by the present inventor.

FEDERALLY SPONSORED RESEARCH

Not Applicable

SEQUENCE LISTING OR PROGRAM

Not Applicable

BACKGROUND

1. Field

The present invention generally relates to water soluble bath capsules containing a bath oil or soap based bath soak that consists of a child's favorite scent such a candies and a plastic toy or figurine, preferably water creatures.

2. Prior Art

Children have always been notorious for avoiding bathing. They are quick to be done if there is nothing there to keep there active imaginations focused. Bath toys encourage children to simulate bath time as a good thing and playing with toys during bath time creates a whole new adventure.

Children love to play with toys in the bath and especially ones that have an element of surprise that includes a favorite bath scent such as a favorite candy and there favorite figurine or toy.

Many toys are used in conjunction with water to provide entertainment such as boats, floats etc. In addition, other toys have been developed which utilize the combination of mystery in conjunction with water.

There have been other products developed utilizing a gelatin or other type of capsule, similar to a pharmaceutical capsule, containing a compressed sponge-like material that is shaped like an animal that is released once the capsule is dissolved in water. There is no bathing element released from these capsules, only the toy.

Swartz in U.S. Pat. No. 2,677,913 in which a figurine was partially embedded. The head and feet protrude from opposite ends of the soap, attempted to entice children to play with soap, but was hidden until the soap was used up and the whole figure would be exposed. It would take the child a long time to use the soap to finally get to the toy, thus minimizing the interest.

RE 38,946 relates to a child's toy and soap assembly that comprises a small toy or figurine located within a body of transparent soap with a soap container that matches the shape of the toy. It will take the child a long time to finally reach the toy thus losing the focus of the child.

Dorfman in U.S. patent Ser. No. 07/907,498 relates to a toy and a dissolvable outer package. There is no bath soak for further enjoyment while bathing. The smell of cotton candy or bubble gum or any favorite candy makes a bath much more fun.

A need exists for the convenience of a drop in type toy and bath soak for an enhanced and immediate entertainment for the child while bathing as well as an educational aspect for learning about the different creatures that inhabit the water.

SUMMARY

The purpose of the invention is to get children to have fun while bathing and to learn about the different creatures that inhabit the water. In addition to having a fun bathing experience, the child will love the smell of his favorite bath scents such as cotton candy, bubble gum, watermelon, etc. Parents will love the ease of dropping in these water soluble capsules as well as the children watching the toy escape from their water soluble container for their enjoyment.

The toy may or may not be seen from the capsule giving an element of surprise. The toy is large enough that it cannot be swallowed by a child.

Child Safe Size

It is an object of the present invention to insure that all toys or figurines fully comply with present child safety standards as to the size of the toy, its composition, and appendages. The size of the toy will not fit into a circular tube with an inside diameter of ¾ of and inch or less.

DRAWINGS

Figures

FIG. 1 is a perspective view of the water soluble membrane 5 comprising of a liquid bath soap, or bath oils 6 that is transparent and can be tinted in color or clear. The toy or figurine 7 is encapsulated within the water soluble membrane. The outer water soluble membrane dissolves leaving bath bubbles and or bath soak and a toy. The toy is released from the water soluble membrane.

FIG. 2 shows a turtle 10 encapsulated within a water soluble membrane 8 comprising of a liquid bath soap, bath oil substance 9 that is transparent or tinted in color. The turtle is released along with the bath soap or bath oil substance once the outer membrane has dissolved in the bath water.

FIG. 3 shows the toy assembly encapsulating a diver 13 comprising of clear or tinted in color, transparent liquid bath soap or bath oils 12 within a water soluble membrane 11. The membrane dissolves in the bath water leaving the turtle and the bath bubbles or bath oils for soaking.

DRAWINGS - Reference Numerals

| | | | |
|---|---|---|---|
| 5 | water soluble membrane | 6 | liquid bath oils or soap |
| 7 | toy figurine | 8 | water soluble membrane |
| 9 | liquid bath oils or soap | 10 | toy figurine |
| 11 | water soluble membrane | 12 | liquid bath oils or soap |
| 13 | toy figurine | | |

DETAILED DESCRIPTION

The preferred embodiment of the invention consists of an outer water soluble membrane encapsulating a waterproof figurine, or toy which is suspended in a liquid soap or liquid bath oil that is transparent or tinted in color. The water soluble membrane can be made from a gelatin-type substance similar to medicinal capsules. Another way to make the water soluble membrane is by using poly vinyl alcohol. The figurine or toy can be visible or concealed through the outer water soluble membrane. The membrane dissolves in water leaving the toy or figurine and the liquid soap for making bath bubbles or bath oils for a bath soak. Children will love watching the toy being released into the bath while bathing. The child can collect the different figurines or toys for further enjoyment in or out of the bath. The manufacturing process will be the same as a bath bead with an additional step of inserting the figurine or toy. It can also be manufactured using a water soluble capsule or water soluble bag.

Operation

In operation one uses the toy assembly in the bath. The user can add one or two of the toy assemblies to the bath water. When added to the water, 5 effects increase the enjoyment of taking a bath for children.

(1) The toy is visible or concealed within the water soluble membrane comprising of a transparent tinted or clear liquid bath soap or bath oils.
(2) The outer water soluble membrane dissolves in the bath water.
(3) The toy is released into the bath water.
(4) The liquid bath soap or bath oils make a bubble bath or a relaxing soothing bath once the outer membrane is fully dissolved leaving only the toy and a wonderful bath.
(5) The child can collect all the different animals for later enjoyment in or out of the bath.

I claim:

1. An encapsulated bath capsule consisting of;
    (a) an outer water soluble membrane selected from the group consisting of gelatin and polyvinyl alcohol;
    (b) a transparent encapsulated liquid selected from the group consisting of soap and oils;
    (c) a waterproof toy or figurine having an inter diameter of no more than ¾ inch and enclosed in said water soluble membrane surrounded by said liquid;
    (d) wherein, said outer soluble membrane is transparent and dissolves in water leaving bath bubbles and a toy or figurine.

2. A water soluble membrane as described in claim 1 in which the membrane is colored or tinted.

3. A water soluble membrane as described in claim 1 in which the membrane is made of gelatin composition.

4. A water soluble membrane as described in claim 1 in which the membrane is made of polyvinyl alcohol.

5. A water soluble membrane as described in claim 1 wherein said bath soap or bath oil is scented.

6. A water soluble membrane as described in claim 1 wherein said bath soap or bath oil contains sparkles.

* * * * *

UNITED STATES PATENT AND TRADEMARK OFFICE
CERTIFICATE OF CORRECTION

Page 1 of 1

PATENT NO. : 8,394,750 B1
APPLICATION NO. : 12/928753
DATED : March 12, 2013
INVENTOR(S) : Robin Forgash It is certified that error appears in the above-identified patent and that said Letters Patent is hereby corrected as shown below:

In the Claims:

Column 3:
Claim 1, component (c), cancel "more" should be changed to --less--.

Signed and Sealed this
Thirteenth Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,394,750 B1  
APPLICATION NO. : 12/928753  
DATED : March 12, 2013  
INVENTOR(S) : Robin Forgash Page 1 of 1

It is certified that error appears in the above-identified patent and that said Letters Patent is hereby corrected as shown below:

In the Claims:

Column 4, line 4 (Claim 1, line 7) "more" should be changed to --less--.

This certificate supersedes the Certificate of Correction issued August 13, 2013.

Signed and Sealed this  
Third Day of September, 2013

Teresa Stanek Rea  
*Acting Director of the United States Patent and Trademark Office*